US00PP32545P2

(12) United States Plant Patent
Hachmann

(10) Patent No.: US PP32,545 P2
(45) Date of Patent: Dec. 1, 2020

(54) ***DASIPHORA* PLANT NAMED 'HACHBIANCA'**

(50) Latin Name: ***Dasiphora fruticosa* subsp. *fruiticosa***
Varietal Denomination: Hachbianca

(71) Applicant: Holger Hachmann, Barmstedt (DE)

(72) Inventor: Holger Hachmann, Barmstedt (DE)

(73) Assignee: HACHMANN BAUMSCHULEN, Barmstedt (DE)

( * ) Notice: Subject to any disclaimer, the term of this patent is extended or adjusted under 35 U.S.C. 154(b) by 0 days.

(21) Appl. No.: 16/873,309

(22) Filed: Mar. 18, 2020

(51) Int. Cl.
*A01H 5/02* (2018.01)
*A01H 6/74* (2018.01)

(52) U.S. Cl.
USPC ..... Plt./237

(58) Field of Classification Search
USPC ..... Plt./226, 237
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Dasiphora* plant named 'Hachbianca' that is characterized by its very compact plant shape, its a low and flat plant shape, its foliage that is dark green-grey in color, its prolific and long blooming habit, and its flowers that are pure white in color.

2 Drawing Sheets

Botanical classification: *Dasiphora fruticosa* subsp. *fruiticosa.*
Variety denomination: 'Hachbianca'.

CROSS REFERENCE TO A RELATED APPLICATIONS

This application is related to a European plant breeders' rights application filed on May 23, 2016, application No. 2016/1237 and a Canadian plant breeders' rights application filed on Dec. 4, 2019, application No. 19-10052. There have been no offers for sale anywhere in the world prior to the effective filing date of this Application and no accessibility to one of ordinary skill in the art could have been derived from the printed plant breeders' rights documents.

BACKGROUND OF THE INVENTION

The present invention relates to a new and distinct cultivar of *Dasiphora fruticosa* subsp. *fruiticosa* (syn. *Dasiphora fruticosa*, syn. *Potentilla fruticosa*). The new cultivar will be referred to hereafter by its cultivar name, 'Hachbianca'. 'Hachbianca' is a new cultivar of deciduous shrub grown for landscape use.

The new cultivar arose from a cross made by the Inventor in Barmstedt, Germany in June 2010 between *Dasiphora fruticosa* 'Manchu' (not patented) as the female parent and *Dasiphora fruticosa* 'Eisprinzessin' as the male parent (not patented). The Inventor selected 'Hachbianca' as a single unique plant amongst the seedlings that resulted from the above cross in June of 2014.

Asexual propagation of the new cultivar was first accomplished by softwood cuttings by the Inventor in Barmstedt, Germany in July of 2014. Asexual propagation by softwood cuttings has determined that the characteristics of the new cultivar are stable and reproduced true to type in successive generations.

SUMMARY OF THE INVENTION

The following traits have been repeatedly observed and represent the characteristics of the new shrub rose. These attributes in combination distinguish 'Hachbianca' as a unique cultivar of *Dasiphora.*

1. 'Hachbianca' exhibits a very compact plant.
2. 'Hachbianca' exhibits a low and flat plant shape.
3. 'Hachbianca' exhibits foliage that is dark green-grey in color.
4. 'Hachbianca' exhibits a prolific and long blooming habit.
5. 'Hachbianca' exhibits flowers that are pure white in color.

The seed parent of 'Hachbianca' differs from 'Hachbianca' in having a squarrose (square and less flat) plant shape, foliage that is more grey in color and a less floriferous blooming habit. The pollen parent of 'Hachbianca' differs from 'Hachbianca' in having a rounded plant shape, a dwarf but less compact plant habit, and flowers that are cream in color. 'Hachbianca' can also be compared to the *Dasiphora fruticosa* cultivars 'Abbotswood' (not patented) and 'McKay's White' (not patented). 'Abbotswood' and 'McKay's White' are both similar to 'Hachbianca' in having flowers that are white in color. 'Abbotswood' differs from 'Hachbianca' in having a broad and upright plant shape, a much less compact plant habit, foliage that is more grey in color and a shorter flowering period. 'McKay's White' differs from 'Hachbianca' in having a broadly spreading upright plant shape and foliage that is more grey in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure include but may not be limited to website listings by new plants, bloomin' easy, rhs, kordes jungpflanzen, and crocus.

BRIEF DESCRIPTION OF THE DRAWINGS

The accompanying colored photographs illustrate the overall appearance and distinct characteristics of the new *Dasiphora*. The photographs were taken of a 2-year-old plant as grown outdoors in a 15-cm container at a nursery in Stroe, The Netherlands.

The photograph in FIG. 1 provides a side view of a plant of 'Hachbianca' in bloom.

Figure 1:
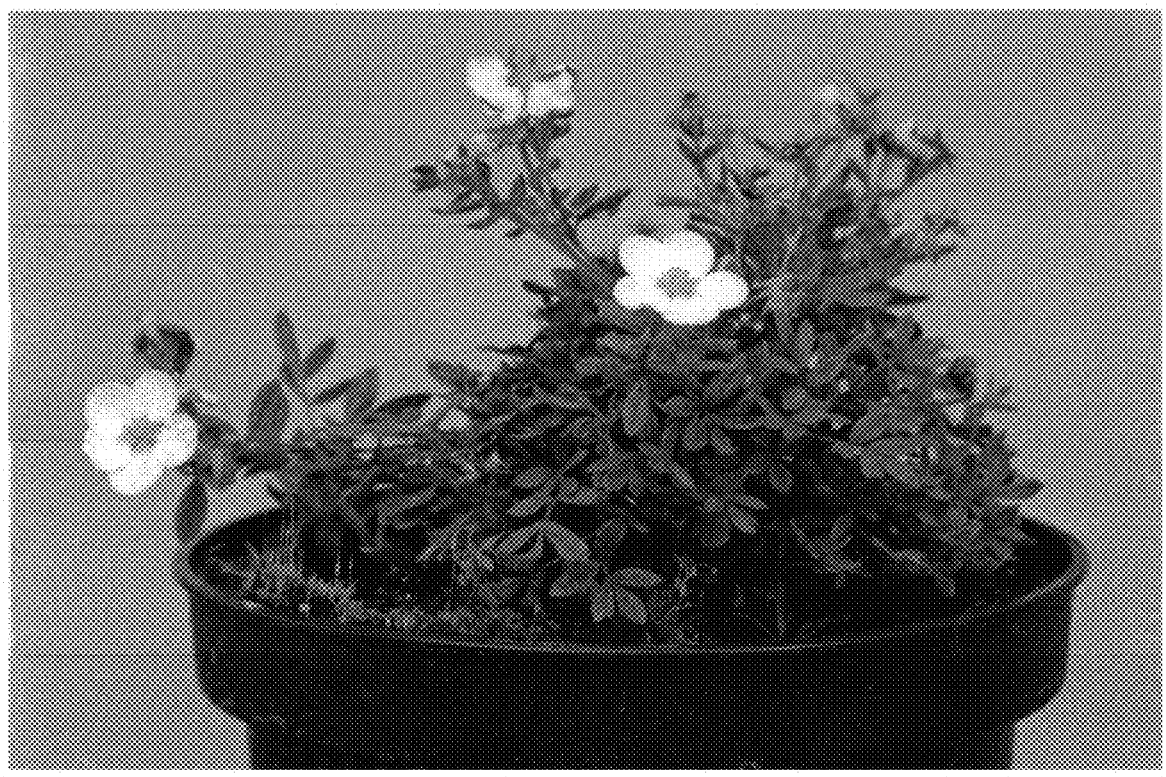
Figure 2:
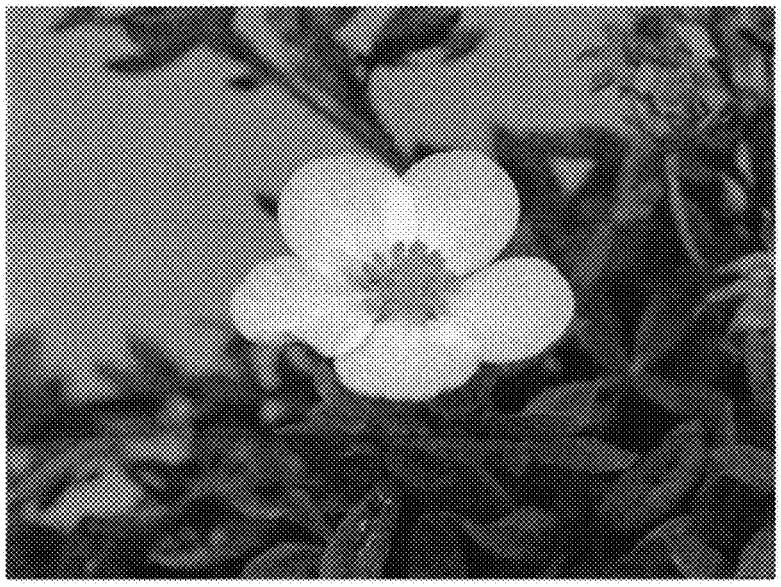

The photograph in FIG. 2 provides a close-up view of a flower of 'Hachbianca'.

Figure 3:
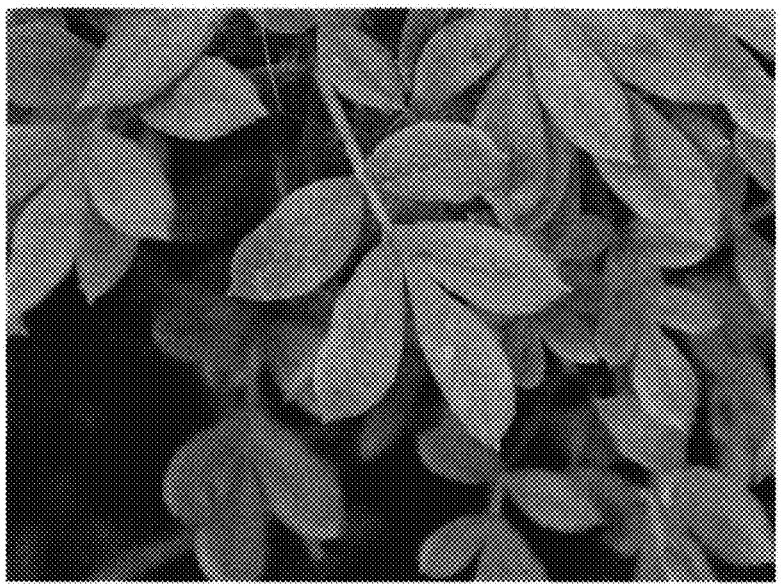

The photograph in FIG. 3 provides a close-up view of the foliage of 'Hachbianca'.

The colors in the photographs are as close as possible with the photographic and printing technology utilized and the color values cited in the detailed botanical description accurately describe the colors of the new *Dasiphora*.

DETAILED BOTANICAL DESCRIPTION

The following is a description of 2-year-old plants as grown outdoors in 15-cm containers in Stroe, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Late spring (May) into late summer (August to early September) in The Netherlands.

*Plant type*.—Deciduous shrub.

*Plant habit*.—Broadly spreading and upright.

*Height and spread*.—An average of 11 cm in height and 16.5 cm in width as a two-year-old plant in a container and reaches 40 cm in height and 50 cm in spread as a mature plant in the landscape.

*Cold hardiness*.—At least in U.S.D.A. Zone 3.

*Diseases and pests*.—No susceptibility or resistance to diseases or pests has been observed.

*Propagation*.—Softwood cuttings.

*Root description*.—Fibrous, 200A.

*Growth rate*.—Moderate.

*Root development*.—Cuttings initiate roots in about 6 weeks and a fully rooted cutting plant is produced in about 3 months.

Branch description:

*Branch shape*.—Rounded.

*Branch color*.—Young; 146D on both surfaces with upper surface of stems tinged 182B, mature wood and bark; 175A.

*Branch surface texture*.—Matte and densely pubescent; covered with short soft hairs an average of 1 mm in length and 156D in color.

*Branching*.—Freely branching.

*Branch size*.—An average of 6.5 cm in length and 1 mm in diameter.

*Branch quantity*.—An average of 22 lateral branches.

*Internode length*.—Average of 1.2 cm.

Foliage description:

*Leaves*.—6, compound, tri-foliate, alternate arrangement, oblong in shape, an average of 2.1 cm in length and width, color; young upper surface 138A, young lower surface 138C, mature upper surface NN137C, mature lower surface 138B, both surfaces slightly glossy and moderately pubescent with short adpressed hairs an average of 1 mm in length and NN155D in color, veins; pinnate, top side veins NN137C in color, lower side veins 147D in color.

*Leaflets*.—3 per leaf, central leaflet is trifoliate making the whole leaf imparipinnate with 5 leaflets, obovate in shape, broadly acute apex, obtuse base, entire margins, an average of 1.2 cm in length and 5 mm in width, color; young upper surface 138A, young lower surface 138C, mature upper surface NN137C, mature lower surface 138B, both surfaces slightly glossy and moderately pubescent with short adpressed hairs an average of 1 mm in length and NN155D in color, veins; pinnate, top side veins NN137C in color, lower side veins 147D in color.

*Stipules*.—Ovate in shape, an average of 7 mm in length and 2 mm in width, both sides N199D in color.

*Petioles*.—Petioles; an average of 1.2 cm in length and 0.75 mm in diameter, high strength, color 144B, surface is slightly glossy, petiolules; none.

Inflorescence description:

*Inflorescence type*.—Solitary, terminal and axillary at upper nodes of stems.

*Flower number*.—An average of 4 per main stem, 100 per plant.

*Flower fragrance*.—None.

*Flower longevity*.—About 5 days, self-cleaning.

*Flower type*.—Single, rotate.

*Flower aspect*.—upright to outward.

*Flower size*.—An average of 2.5 cm in diameter and 7 mm in depth.

*Pedicels*.—An average of 1.4 mm in length, 1 mm in diameter, densely pubescent surface, 144C in color, moderate in strength.

*Flower buds*.—Flattened globular in shape, an average of 5 cm in diameter and length, color 144C.

*Sepals*.—10, placed in two whorls, ovate and elliptic in shape, entire margin, color on upper and lowers surface; 144D, an average of 8 mm in length and 3 mm in width, acute apex, cuneate to broadly cuneate base, both surfaces glabrous.

*Petals*.—An average of 5 per flower, broad obovate to nearly orbicular in shape, glabrous and matte upper and lower surface, margin entire, cuneate base, obtuse apex, an average of 1.1 cm in length and width, color when opening and fully open upper surface; NN155B to NN155C, color when opening and fully open lower surface; NN155D.

*Calyx*.—Rotate, very slightly reflexed, 3 mm in length, 1.7 cm in diameter.

Reproductive organs:

*Pistils*.—Average of 35, 2 mm in length, stigma; sessile, diffuse in shape, 1 mm in length and 151C in color, style; average of 1 mm in length, 150B in color, ovary; 145A in color, densely covered with short hairs an average, of 0.75 mm in length, 155A in color.

*Stamens*.—30 per flower, filaments; average of 2 mm in length and 145C in color, anthers; average of 1 mm in length and 0.9 mm in width, basifixed, broadly ovate and flattened in shape, 11A in color, pollen; low in quantity, 12C in color.

*Fruit and seed*.—Have not been observed to date.

It is claimed:

1. A new and distinct cultivar of *Dasiphora* plant named 'Hachbianca' as herein illustrated and described.

* * * * *